United States Patent
Sekine

[11] Patent Number: 6,037,170
[45] Date of Patent: Mar. 14, 2000

[54] APPARATUS FOR CULTURING MICROALGAE

[76] Inventor: Toshirou Sekine, 978-1, Ohnohara, Chichibu-Shi, Saitama-Ken, Japan

[21] Appl. No.: 09/343,720

[22] Filed: Jun. 30, 1999

Related U.S. Application Data

[63] Continuation of application No. PCT/JP97/04764, Dec. 24, 1997.

[51] Int. Cl.[7] .................................................. C12M 3/00
[52] U.S. Cl. ................................... 435/292.1; 435/293.1; 47/1.4; 47/DIG. 6
[58] Field of Search ............................. 435/286.5, 289.1, 435/292.1, 293.1; 47/60, 1.4, DIG. 6

[56] References Cited

U.S. PATENT DOCUMENTS

| | | | |
|---|---|---|---|
| 3,468,057 | 9/1969 | Buisson et al. | 435/292.1 |
| 3,955,317 | 5/1976 | Gudin | 435/292.1 |

FOREIGN PATENT DOCUMENTS

| | | |
|---|---|---|
| 62-220183 | 9/1987 | Japan . |
| 3-251169 | 11/1991 | Japan . |
| 6-90735 | 4/1994 | Japan . |
| 6-350119 | 12/1994 | Japan . |
| 7-8264 | 1/1995 | Japan . |
| WO98/29531 | 7/1998 | WIPO . |

Primary Examiner—David A. Redding
Attorney, Agent, or Firm—Jacobson, Price, Holman & Stern, PLLC

[57] ABSTRACT

An apparatus for culturing microalgae is characterized by comprising:

(1) a waterway a to be filled with a suspension containing a culture solution and microalgae and adapted to be irradiated with sun beams while being held in contact with ambient air;

(2) an upper hermetically sealed storage tank b for storing said suspension to avoid any contact between the latter and ambient air, said storage tank being provided with a deaeration and a switch valve;

(3) an aeration pipe c arranged and apertured in the storage tank b for feeding pressurized gas into the storage tank b; and (4) a pressurized gas feeder d;

the upstream end and the downstream end of the waterway a and the storage tank b being linked at the bottom of the storage tank b by way of a water conduit f to form an endless waterway; the upstream end and the downstream end of the waterway a and the storage tank b being linked at the bottom of the storage tank b so as to allow pressurized gas fed through the aeration pipe c to burst out from the bottom of the storage tank b toward the upstream end of the waterway a through the inside of the storage tank b.

8 Claims, 6 Drawing Sheets

APPARATUS FOR CULTURING MICROALGAE

This is a continuation of PCT Application No. PCT/JP97/04764, filed Dec. 24, 1997.

TECHNICAL FIELD

This invention relates to an apparatus for culturing microalgae such as chlorella for proliferation.

BACKGROUND ART

Generally, microalgae are cultured in flat and shallow ponds constructed outdoors such as culture ponds for chlorella and oxidation ponds for treating waste water. The use of such ponds is, however, accompanied by problems including;

(1) high cost of water agitation,
(2) a large heat loss from the large water surface particularly at night in cold districts, cooling the culture solution of the pond and reducing the rate of reproduction of microalgae in there and
(3) invasion and proliferation of predators such as daphnia and rotifer that cannot be prevented from occurring without using chemicals to a large extent.

Remarkable developments can be expected in the technological fields of production of edible algae that can reproduce proteins at a rate of more than a hundred times of soy beans, treatment of waste water by means of algae accompanied by utilization of the latter as by products and fixation of carbon dioxide by means of algae as countermeasure for the warming earth. From this point of view, the inventors of the present invention applied for patent for an apparatus for culturing photosynthetic microbes and a method for operating the same also invented by the inventors of the present invention (now filed as Japanese Patent Application Laid-Open No. 4-283146). The present invention relates to this prior art invention.

DISCLOSURE OF THE INVENTION

Therefore, it is the object of the present invention to provide an apparatus for culturing microalgae that can bypass the above three problems of (1), (2) and (3) and can reduce the cost of agitation and prevent the cooling of culture liquid and proliferation of daphnia and rotifer so that fin algae may be cultured stably and efficiently.

According to the invention, the above object is achieved by providing an apparatus for culturing microalgae characterized by comprising:

(1) a waterway a to be filled with a suspension containing a culture solution and microalgae and adapted to be irradiated with sun beams while being held in contact with ambient air;
(2) an upper hermetically sealed storage tank b for storing said suspension to avoid any contact between the latter and ambient air, said storage tank being provided with a deaeration and a switch valve;
(3) an aeration pipe c arranged and apertured in the storage tank b for feeding pressurized gas into the storage tank b; and
(4) a pressurized gas feeder d the upstream end and the downstream end of the waterway a and the storage tank b being linked at the bottom of the storage tank b by way of a water conduit f to form an endless waterway; the upstream end and the downstream end of the waterway a and the storage tank b being linked at the bottom of the storage tank b so as to allow pressurized gas fed through the aeration pipe c to burst out from the bottom of the storage tank b toward the upstream end of the waterway a through the inside of the storage tank b.

Now, the present invention will be described in greater detail by referring to the accompanying drawings that illustrate preferred embodiments of the invention.

BEST MODE FOR CARRYING OUT THE INVENTION

Figure 1:
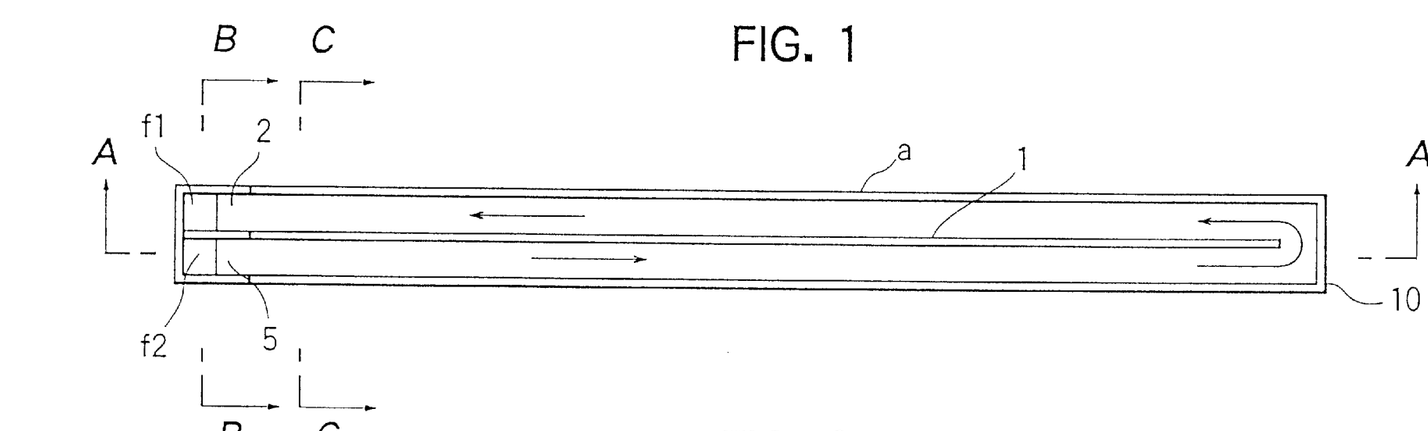
FIG. 1 is a schematic plan view of an embodiment of apparatus according to the invention.
Figure 2:
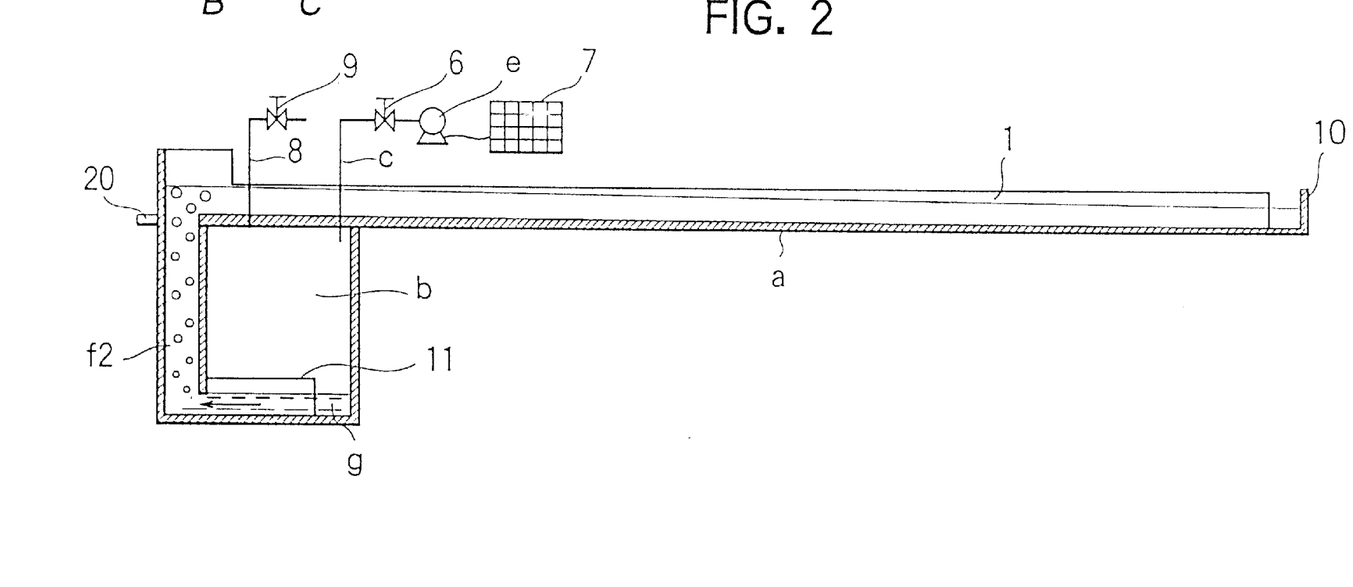
FIG. 2 is a schematic longitudinal cross sectional view taken along line A—A in FIG. 1.
Figures 3, 4, 5:
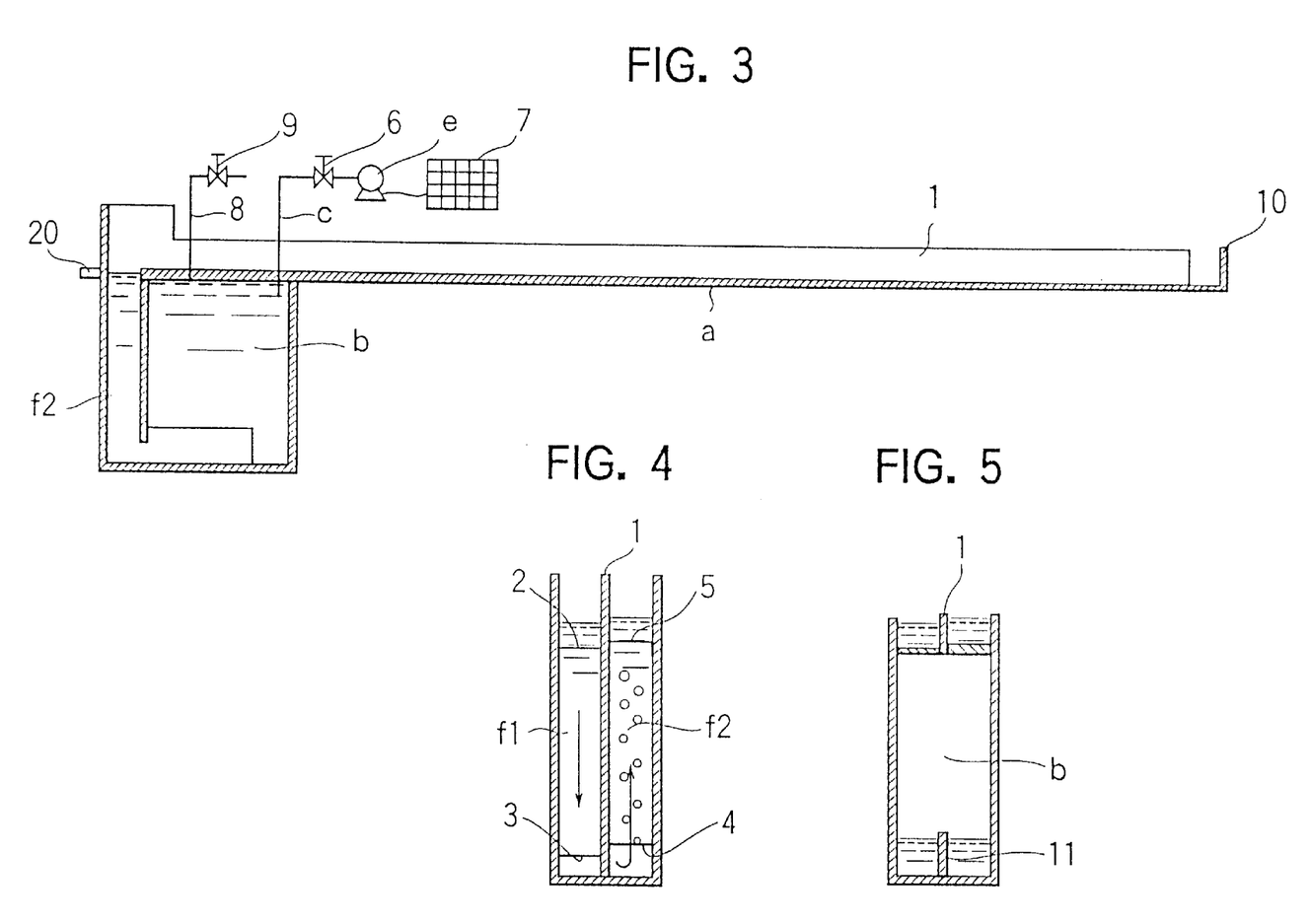
FIG. 3 is a schematic longitudinal cross sectional view taken also along ling A—A FIG. 1 and showing a state where the suspension in the waterway a is moved into the storage tank b.
FIG. 4 is a schematic longitudinal cross sectional view taken along line B—B in FIG. 1.
FIG. 5 is a schematic longitudinal cross sectional view taken along line C—C in FIG. 1.
Figure 6:
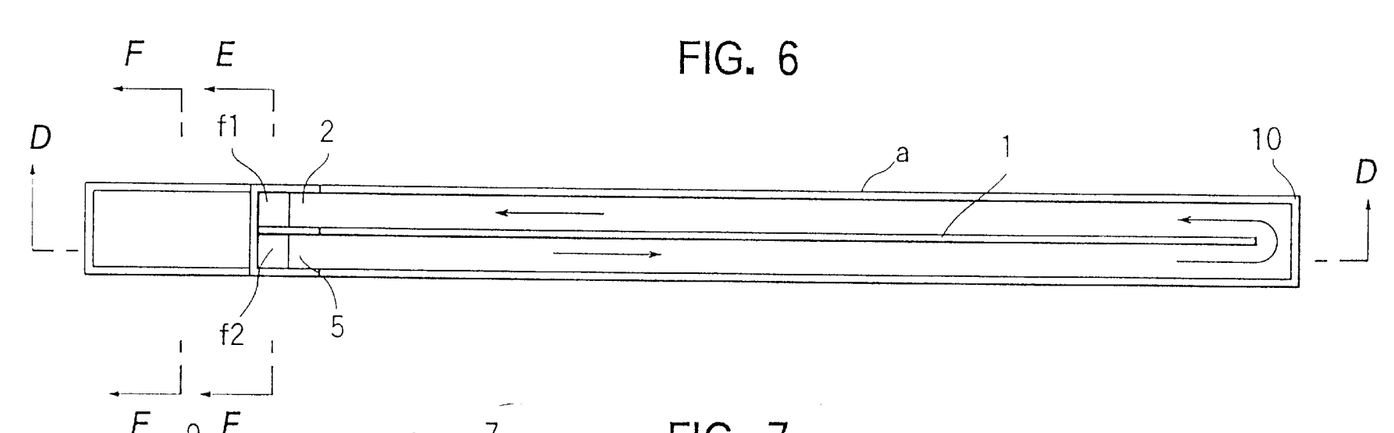
FIG. 6 is a schematic plan view of another embodiment of apparatus according to the invention.
Figure 7:
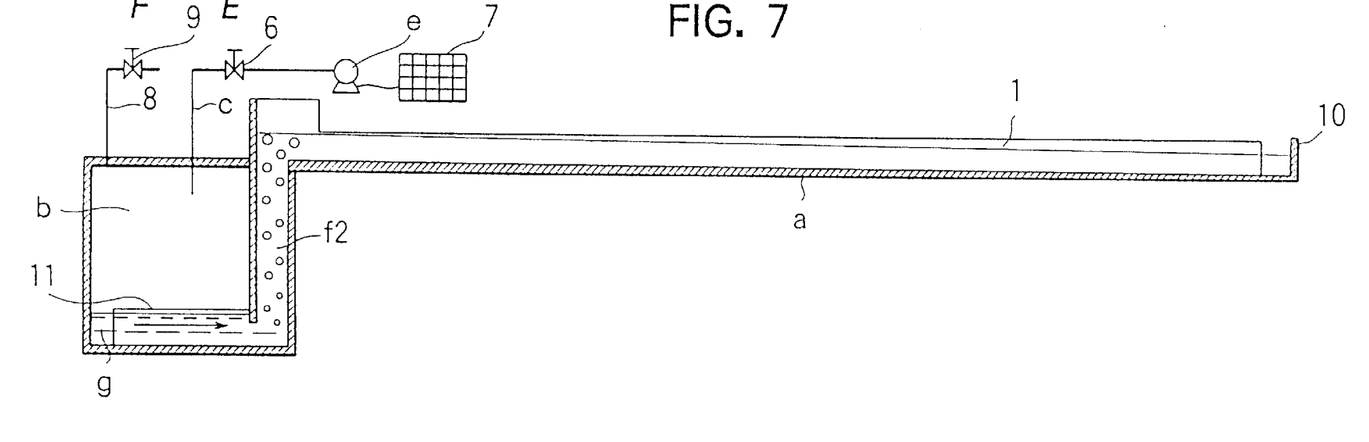
FIG. 7 is a schematic longitudinal cross sectional view taken along line D—D in FIG. 6.
Figures 8, 9, 10:
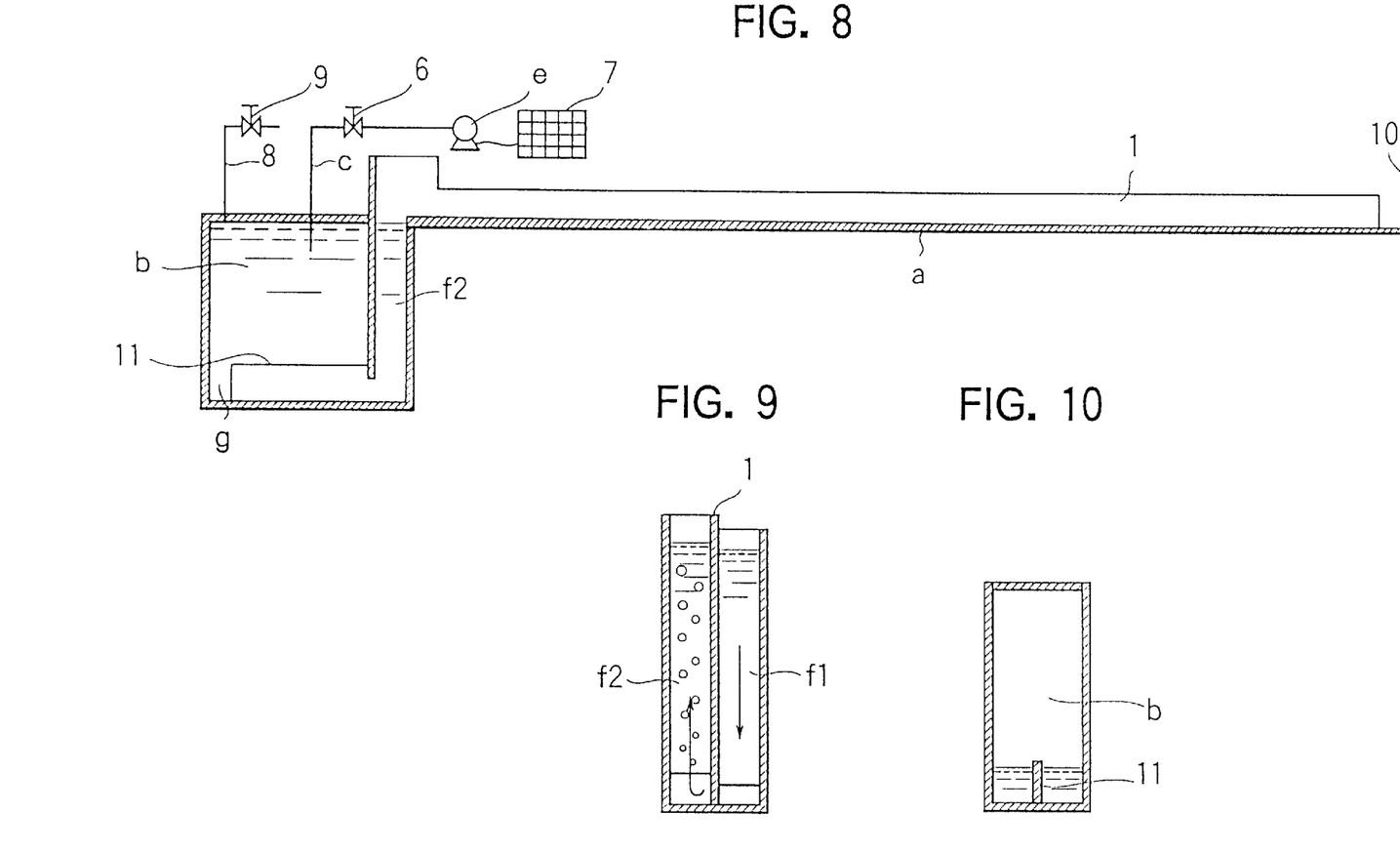
FIG. 8 is a schematic longitudinal cross sectional view taken also along line D—D in FIG. 6 and showing a state where the suspension in the waterway a is moved into the storage tank b.
FIG. 9 is a schematic longitudinal cross sectional view taken along line E—E in FIG. 6.
FIG. 10 is a schematic longitudinal cross sectional view taken along line F—F in FIG. 6.
Figure 11:
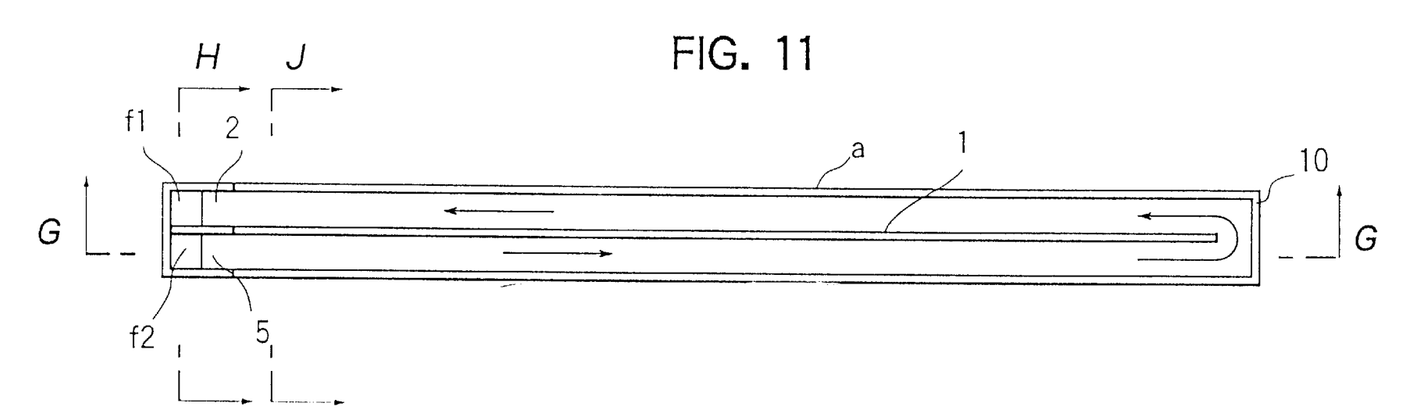
FIG. 11 is a schematic plan view of still another embodiment of apparatus according to the invention.
Figure 12:
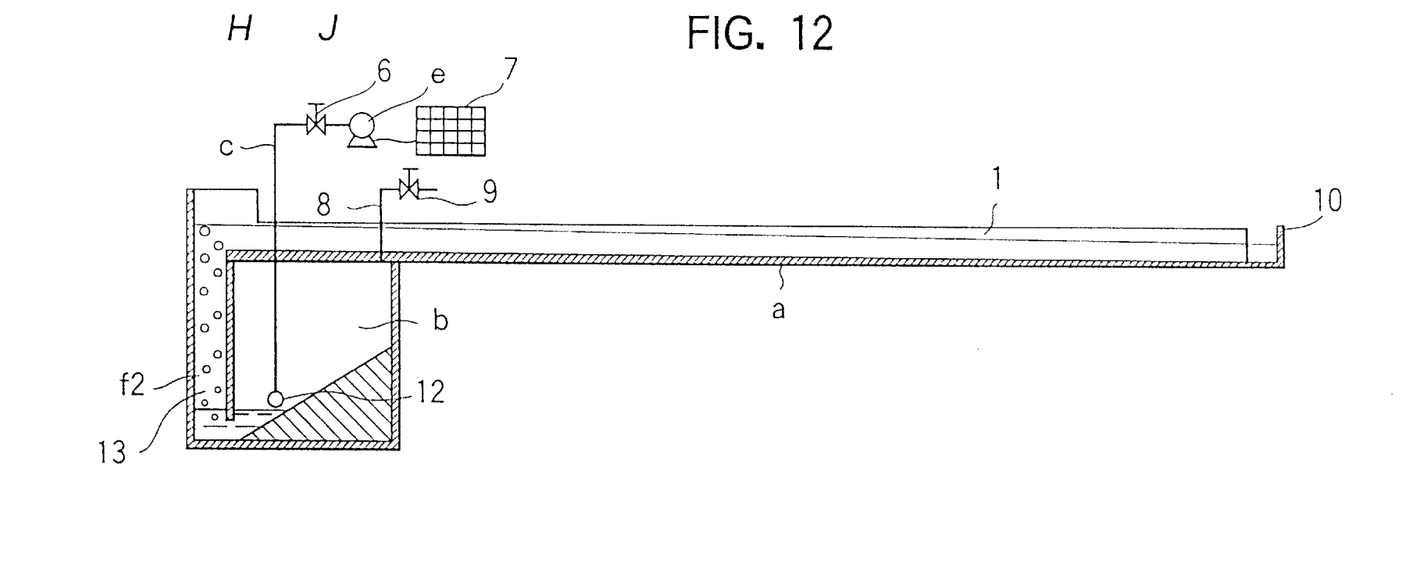
FIG. 12 is a schematic cross sectional view taken along line G—G in FIG. 11.
Figures 13, 14, 15:
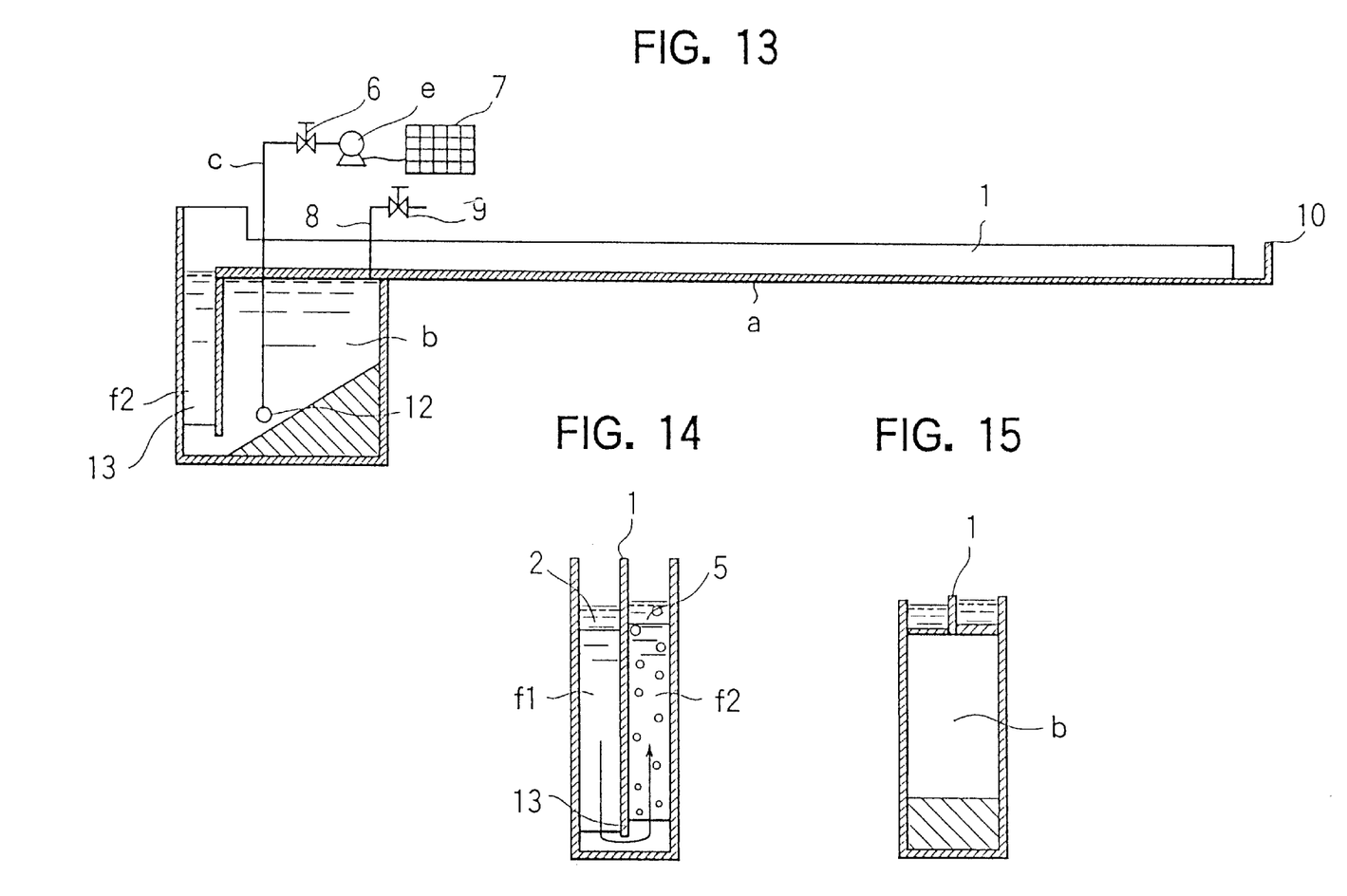
FIG. 13 is a schematic longitudinal cross sectional view taken also along line G—G in FIG. 11 and showing a state where the suspension in the waterway a is moved into the storage tank b.
FIG. 14 is a schematic longitudinal cross sectional view taken along line H—H in FIG. 11.
FIG. 15 is a schematic longitudinal cross sectional view taken along line J—J in FIG. 11.

FIGS. 1 through 5 schematically illustrate a preferred embodiment of the invention. FIG. 1 is a schematic plan view and FIGS. 2 and 3 are schematic longitudinal cross sectional views taken along line A—A in FIG. 1, whereas FIG. 4 is a schematic longitudinal cross sectional view taken along line B—B in FIG. 1 and FIG. 5 is a schematic longitudinal cross sectional view taken along line C—C in FIG. 1. This embodiment comprises a shallow waterway a adapted to be irradiated with sun beams from above and a storage tank b arranged below it.

The waterway a is folded into a pair of parallel tracks separated by a partition wall 1 and its downstream end 2 is linked to the bottom of the storage tank b by way of a water conduit f extending vertically downward therefrom and then to the upstream end 5 of the waterway a by way of inlet port 3 of the storage tank b, a water conduit g arranged at the bottom of the storage tank b and deminuted by a partition wall 11, outlet port 4 of the storage tank b and another conduit f2 extending vertically upward therefrom to form an endless waterway. When the storage tank b is filled with a culture solution and any excessive part thereof is left in the shallow waterway a, the residual culture solution in the waterway a contacts with ambient air to allow small creatures such as protozoa, daphnia and rotifer living in there to respire and reproduce actively as they eat microalgae. Therefore, a water discharge port 20 is arranged at the water conduit f1 and provided with a switch valve (not shown) in order to avoid any residual culture solution remaining in the waterway a. Alternatively, the water discharge port 20 may be arranged at the water conduit f2.

An aeration pipe c is arranged in and above the storage tank b and made open to the latter in order to introduce compressed air that may or may not contain carbon dioxide to an excessive extent into the storage tank b. The aeration pipe c is linked to a blower e provided with a DC motor operating as pressurized air feeder d byway of a valve 6. A solar battery 7 is arranged to supply power to the blower e. The storage tank b is arranged below the waterway a to store a suspension containing microalgae and the culture solution and provided at an upper portion thereof with a deaeration pipe 8 and a valve 9 for drawing out air. The upper end of the outlet port 4 of the storage tank b is located above the upper end of the inlet port 3 of the storage tank b. The bottom of the waterway a is sloped downwardly from the upstream end 5 toward the downstream end 2 thereof.

As the valve 9 is closed and pressurized gas is introduced through the aeration pipe c, the suspension will be made present throughout the endless waterway formed by the waterway a1, the water conduit f1, the water conduit g and the water conduit f2 as shown in FIG. 2. When the introduction of pressurized gas is suspended and the valve 9 is opened, then the suspension becomes contained within the water conduit f1, the water conduit g, the water conduit f2 and the storage tank b as seen from FIG. 3.

As the sun rises, the valve 9 and the switch valve (not shown of the water discharge port 20 are closed and the blower e is driven to operate by the power fed from the solar battery 7. Gas is then supplied to the storage tank b by way of aeration pipe c at a controlled flow rate so that the suspension in the storage tank b is forced to flow into the waterway a. As gas is further supplied to the storage tank b, the gas already stored in the storage tank b is partly forced to move out through the storage tank outlet port 4 and go into the water conduit f2. Then, a large volume of gas suddenly bursts out downwardly in the water conduit f2 as a result of the wave generated by gas along the gas/liquid interface to raise the liquid level of the water conduit f2 and lower that of the water conduit f1 so that consequently the liquid flows from the upstream side toward the downstream side and produces a large wave to agitate the suspension. While the liquid level of the storage tank b may be raised above the upper end of the storage tank outlet port 4 temporarily, the gas/liquid interface will fall down once again as the supply of pressurized gas continues so that the above burst of gas will be repeated cyclically with a constant cycle period. Thus, the suspension is agitated to encourage the microalgae in there to reproduce vigorously as the suspension is irradiated with sun beams.

When the sun sets, the operation of the blower e will be terminated and the valve 9 is opened to allow the suspension to move into the storage tank b and eventually stored in the water conduit f1, the water conduit f2 and the storage tank b. If the storage tank b is filled with the suspension and any residual portion thereof is left in the waterway a, the switch valved (not shown) of the water discharge port 20 is opened to discharge the residual suspension in order to suppress any possible survival and proliferation of predator microbes living on microalgae such as protozoa, daphnia and rotifera. Since the stored suspension scarcely has a surface area that contacts with ambient air and, particularly, the suspension in the storage tank b does not absolutely contact with air, it gradually becomes anaerobic as the microbes remaining therein respire and consume oxygen to suppress any possible survival and proliferation of the predator microbes living on microalgae such as protozoa, daphnia and rotifer and reduce the degree by which the suspension is cooled at night. The above operation is repeated every day as far as the process of culturing microalgae continues so that eventually microalgae will no longer be taken by microbes to provide a high density culture of microalgae in a highly efficient and stable manner.

While the storage tank b may be arranged not below the waterway a but in an area separated from the waterway a, the arrangement of the storage tank b below the waterway a can minimize the area of the installation site. However, the location of arrangement of the storage tank b is not limited to the position right below the waterway a and it may alternatively be arranged beside the waterway a as shown in FIGS. 6 through 10.

While the aeration pipe c for introducing air that may or may not contain carbon dioxide to an excessive extent is apertured in a upper portion of the storage tank b in the embodiment of FIGS. 1 through 5, it may be apertured at any position within the storage tank b. In the case of an organic culture of microalgae, air supplied through the aeration pipe c may or may not container carbon dioxide to an excessive extent, whereas, in the case of an inorganic culture of microalgae, air supplied through the aeration pipe c contains carbon dioxide to an excessive extent.

The upper end of the storage tank outlet port 4 is located above the upper end of the storage tank inlet port 3. Therefore, the gas in the storage tank b bursts out into the water conduit f2 so that the suspension flows from the upstream side to the downstream side in the storage tank b and becomes agitated. Then, the blower e forces the suspension to move from the waterway a to the storage tank b and, at the same time, agitates the suspension in the waterway a in a highly efficient way.

While waterways such as the waterway a of this embodiment are typically formed by using concrete or cement blocks in conventional apparatus of the type under consideration, low cost waterproof sheets such as vinylchloride sheets fabricated for agricultural applications may be used for the waterway a of an apparatus according to the invention because if any liquid leakage occurs, the suspension in the waterway a can be contained in the storage tank b and the leak can be remedied quickly. Of course, the water conduits f1 and f2, the storage tank b and the bent section 10 should be formed by using a hard and rigid material such as concrete, cement blocks or hard synthetic resin but the remaining portions of the water conduits of the apparatus may be water-proofed by means of low cost sheets such as vinylchloride sheets. All the exposed components of the bottom of the waterway a are preferably directed from the upstream end toward the downstream end in a streamlined fashion so that liquid may flow smoothly thereon and sedimentation and putrefaction of algae may be minimized with minimal agitation cost.

FIGS. 11 through 15 shows a still another embodiment of the present invention, where the storage tank b is formed differently if compared with its counterparts of the first and second embodiments. In this embodiment, the suspension moves from the water conduit f1 toward the water conduit f2 below partition wall 13 without passing by the bottom of the storage tank b during the daytime when algae are nourished. Additionally, the aeration pipe c is apertured at the bottom of the storage tank b so that the suspension in the storage tank b is agitated when it is forced out into the waterway a, although it will be difficult to completely eliminate sedimentation and putrefaction of algae if the depth of the suspension is small because it will then not be agitated satisfactorily. To the contrary, in the case of the embodiment of FIGS. 1 through 5, the downstream end 2 is linked to the bottom of the storage tank b by way of the water conduit f1 extending vertically downward and further to the upstream end 5 by way of the storage tank inlet port 3, the water conduit g arranged at the bottom of the storage tank b and deminuted by the partition wall 11, the storage tank outlet port 4 and the water conduit f2 extending from the outlet port 4 vertically upward to produce an endless waterway so that the suspension in the storage tank b can be agitated even at the bottom and hence sedimentation and putrefaction of algae can easily be prevented from occurring.

While a solar battery is used as power source in this embodiment, a commercial power source may alternatively be used for the purpose of the invention. However, the apparatus can be activated and deactivated automatically at the sun rise and at the sun set respectively to reduce the cost of controlling the operation of the apparatus if a solar battery is used as power source and the operation of the valve 9 is controlled appropriately.

The results of experimental operations obtained in the following examples will be summarily described below.

EXAMPLE 1

An experiment on the thermal insulation effect of the present invention was conducted during the period from Jan. 16 to Feb. 3, 1996, using a pair of apparatus as shown in FIGS. 1 through 5. A commercially available power source was used. In apparatus No. 1, a suspension was made to circulate through the waterway a (length: 22 m, width: 0.9, lateral wall: formed by arranging a single layer of 10 cm high concrete blocks, liquid depth: 12 cm) from 8 o'clock in the morning until 5 o'clock in the evening every day and the suspension was stored in the storage tank b (lateral wall: formed by arranging 9 layers of 10 cm high concrete blocks) from 5 o'clock in the evening until 8 o'clock in the morning of the next day. In apparatus No. 2, a similar suspension was made to circulate through the waterway a throughout the period of the experiment. The liquid temperature was observed at 1 o'clock in the afternoon every day during the period of experiment. As a result, the liquid temperature of apparatus No. 1 was found to be higher than that of apparatus No. 2 to prove the thermal insulation effect of the present invention.

EXAMPLE 2

Chlorella was nourished by using waste water from a pigpen as culture solution. The suspension was distributed to apparatus No. 1 and apparatus No. 2 when protozoa, daphnia and rotifer were observed in it and it became discolored. Then, liquid obtained by leaving waste water from the pigpen in a stationary state to allow precipitation and diluting the supernatant with clean water to a volume of 100 times of the original volume was added thereto. For the culture of apparatus No. 1, the suspension was made to circulate through the waterway a during the day time and stored in the storage tank b at night. For the culture of apparatus No. 2, on the other hand, the suspension was made to circulate through the waterway a all the time throughout the period of experiment. A commercial power source was used in this example. When observed through a microscope at the end of the experiment, it was found that the number of individuals of protozoa, daphnia and rotifer had been reduced and the suspension regained it green color in apparatus No. 1, whereas the number of protozoa, daphnia and rotifer had not been not reduced and the suspension remained transparent for about one month after the experiment. Additionally, in apparatus No. 1, the culture of chlorella continued to thrive stably after the experiment as diluted waste water from the pigpen was added thereto.

An apparatus according to the invention can be used not only for producing microalgae such as chlorella but also for culturing photosynthetic microbes and for treating urban waste water by means of microalgae as in high speed oxidation ponds.

Industrial Applicability

As described in detail above, an apparatus according to the invention is characterized in that it comprises a waterway a for encouraging microalgae to proliferate and a storage tank b for thermally isolating the suspension contained in it and suppressing survival and reproduction of predator microbes living on microalgae such as protozoa, daphnia and rotifer and its operation of causing the suspension to move between the waterway a and the storage tank b and can be controlled by simply activating or deactivating a pressurized gas feeder d that mobilizes and agitates the suspension. The advantages of an apparatus according to the present invention include:

(1) that it can prevent the suspension from being cooled to a large extent and maintain the rate of reproduction of microalgae to a high level;

(2) that it can prevent predator microbes such as protozoa, daphnia and rotifer living on microalgae from proliferating in the suspension; and (3) that the suspension can be made to flow and agitated efficiently.

Therefore, an apparatus according to the invention can culture microalgae on a stable and efficient basis.

What is claimed is:

1. An apparatus for culturing minute algae, characterized by comprising:

a horizontal flow path for containing liquid and allowing it to be irradiated with sun beams and held in contact with ambient air, said flow path being substantially horizontal and having a first flow path end and a second flow path end;

a first vertical flow path substantially vertical and communicating with said first flow path end;

a second vertical flow path substantially vertical and communicating with said second flow path end;

a storage tank for storing the liquid contained in said horizontal flow path, said storage tank communicating with said first vertical flow path and said second vertical flow path and being provided with an air discharge mechanism and airtightly closed at the upper end thereof; and a pressurized gas feeder arranged within said storage tank for feeding gas;

the upper limit of the height of the communicating path at the boundary section between said first vertical flow path and said storage tank being made higher than the upper limit of the height of the communicating path at the boundary section of said second vertical flow path and said storage tank.

2. An apparatus for culturing minute algae according to claim 1, wherein a separator section is arranged at the bottom of said storage tank to partly isolate a region communicating with said first vertical flow path and a region communicating with said second vertical flow path.

3. An apparatus for culturing minute algae according to claim 1, wherein said horizontal flow path is formed by water-proof sheets.

4. An apparatus for culturing minute algae according to claim 2, wherein said horizontal flow path is formed by water-proof sheets.

5. An apparatus for culturing minute algae according to claim 1, wherein the power source of said pressurized gas feeder is a solar battery.

6. An apparatus for culturing minute algae according to claim 2, wherein the power source of said pressurized gas feeder is a solar battery.

7. An apparatus for culturing minute algae according to claim 3, wherein the power source of said pressurized gas feeder is a solar battery.

8. An apparatus for culturing minute algae according to claim 1, wherein an liquid overflow discharge port is provided at the first vertical flow path or the second vertical flow path.

* * * * *

UNITED STATES PATENT AND TRADEMARK OFFICE
CERTIFICATE OF CORRECTION

PATENT NO. : 6,037,170
DATED : March 14, 2000
INVENTOR(S) : Toshirou Sekine

It is certified that error appears in the above-identified patent and that said Letters Patent is hereby corrected as shown below:

On the title page, insert the following between lines [22] and "Related U.S. Application Data" :

[30] Foreign Application Priority Data

December 30, 1996 [JP] Japan..............................359971/1996

Signed and Sealed this

Thirty-first Day of July, 2001

Attest:

*Attesting Officer*

NICHOLAS P. GODICI
*Acting Director of the United States Patent and Trademark Office*